United States Patent [19]

Jaynes et al.

[11] Patent Number: 5,773,413
[45] Date of Patent: *Jun. 30, 1998

[54] METHOD OF COMBATING MAMMALIAN NEOPLASIAS, AND LYTIC PEPTIDES THEREFOR

[75] Inventors: Jesse M. Jaynes, Raleigh; Gordon R. Julian, Cary, both of N.C.

[73] Assignee: Demeter Biotechnologies, Ltd., Durham, N.C.

[*] Notice: The term of this patent shall not extend beyond the expiration date of Pat. No. 5,717,064.

[21] Appl. No.: 457,171

[22] Filed: Jun. 1, 1995

Related U.S. Application Data

[63] Continuation of Ser. No. 225,476, Apr. 8, 1994, abandoned, which is a continuation-in-part of Ser. No. 39,620, Jun. 4, 1993, abandoned, Ser. No. 148,889, Nov. 8, 1993, abandoned, and Ser. No. 148,491, Nov. 8, 1993, abandoned.

[51] Int. Cl.[6] .............................. A61K 38/16; C07K 7/08; C07K 14/00
[52] U.S. Cl. ................................. 514/12; 514/13; 514/14; 530/324; 530/326; 530/327
[58] Field of Search .................................. 514/12, 13, 14, 514/21; 530/324, 325, 326, 327

[56] References Cited

U.S. PATENT DOCUMENTS

| | | | |
|---|---|---|---|
| 4,355,104 | 10/1982 | Hultmark et al. | 435/70 |
| 4,520,016 | 5/1985 | Hultmark et al. | 514/12 |
| 4,810,777 | 3/1989 | Zasloff | 530/326 |
| 5,070,188 | 12/1991 | Njieha et al. | 530/324 |
| 5,114,921 | 5/1992 | Zasloff | 530/324 |
| 5,186,166 | 2/1993 | Riggs et al. | 128/203.15 |
| 5,217,956 | 6/1993 | Zasloff et al. | 514/21 |
| 5,221,664 | 6/1993 | Berkowitz et al. | 514/21 |
| 5,411,942 | 5/1995 | Widmer et al. | 514/17 |
| 5,424,290 | 6/1995 | Maloy et al. | 514/13 |

FOREIGN PATENT DOCUMENTS

| | | |
|---|---|---|
| 2047317 | 1/1992 | Canada . |
| 12866 | 11/1990 | WIPO . |
| 00869 | 1/1991 | WIPO . |

OTHER PUBLICATIONS

Science, vol. 256, issued 08 May 1992, Collins, "Cystic Fibrosis: Molecular Biology and Therapeutic Implications", pp. 774–779.

Biochemistry, vol. 7, No. 6, issued Jun. 1968, Means et al, "Reductive Alkylation of Amino Groups in Proteins", pp. 2192–2201.

J. Biol. Chem., vol. 213, No. 23, issued 10 Dec. 1968, Takahashi, "The Reaction of Phenylglyoxal with Arginine Residues in Proteins", pp. 6171–6179.

Jaynes, J.M., et al. "In Vitro Cytocidal Effect of Lytic Peptides on Several Transformed Mammalian Cell Lines", *Peptide Research*, 2: 157–160 (1989).

Jaynes, J. M. "Lytic Peptides Portend an Innovative Age in the Management and Treatment of Human Disease", *Drug News and Perspectives*, 3: 69–78 (1990).

(List continued on next page.)

*Primary Examiner*—Jeffrey E. Russel
*Attorney, Agent, or Firm*—Rothwell, Figg, Ernst & Kurz

[57] ABSTRACT

A method of treating neoplasias, including female mammalian neoplasias such as breast, cervical, uterine, and ovarian neoplasias, as well as other neoplasias including prostatic, dermal, and bronchogenic cancers, comprising delivery of an effective non-naturally occurring, non-cytologically proliferative lytic peptide to an appropriate corporeal site to effectively treat such disease state. Particularly preferred lytic peptide agents include small (23–39 amino acids) amphipathic cationic lytic peptides from the classes of synthetic analog derivatives of mellittin, cecropin, magainin, and defensin peptides, most preferably melittic and defensin peptides from the class of synthetic analogs of melittin, cecropin, maganin, and defensin peptides, most preferably synthetic analogs of melittic and defensin peptides.

7 Claims, 1 Drawing Sheet

OTHER PUBLICATIONS

Akerfeldt, et al. "Synthetic Peptides as Models for Ion Channel Proteins", *Acc. Chem. Res.,* 26: 191–197 (1993).

Reed, W.A., et al. "Enhanced In Vitro Growth of Murine Fibroblast Cells and Preimplantation Embryos Cultured in Medium Supplemented with an Amphipathic Peptide," *Molecular Reproduction and Development* 31: 106–113 (1992).

Arrowood, M.J., et al. "Hemolytic Properties of Lytic Peptides Active Against the Sporozites of Cryptosporidium Parvum," *J. Protozool.* 38: 161s–163s (1991).

Jaynes, J. M. et al. "In Vitro Effect of Novel Lytic Peptides on Plasmodium Falciparum and Trypanosoma Cruzi," *FASEB J.* 2: 2878–2883 (1988).

Graham, M. L. et al. "Cytotoxic Effect of Amphipathic Cationic Lytic Peptides on Human and Murine Cancer Cell Lines", *Proceedings of the American Association for Cancer Research* 35: 410 (1994).

Moore, A. J., et al. "Preliminary Experimental Anti–Cancer Activity of Cecropin B," *Proceedings of the American Association for Cancer Research 35: 410* (1994).

METHOD OF COMBATING MAMMALIAN NEOPLASIAS, AND LYTIC PEPTIDES THEREFOR

CROSS-REFERENCE TO RELATED APPLICATION

This application is a continuation of U.S. application Ser. No. 08/225,476, filed Apr. 8, 1994, now abandoned, which is a continuation-in-part of U.S. applications Ser. No. 08/039,620, filed Jun. 4, 1993, now abandoned; Ser. No. 08/148,889, filed Nov. 8, 1993, now abandoned and Ser. No. 08/148,491, filed Nov. 8, 1993, now abandoned.

BACKGROUND OF THE INVENTION

1. Field of the Invention

The present invention relates to a method of combatting mammalian neoplasias, including specifically female mammalian neoplasias, and to non-naturally lytic peptides and their use in such method.

2. Description of Related Art

Naturally occurring amphipathic peptides play an important if not critical role as immunological agents in insects and have some, albeit secondary, defense functions in a range of other animals. The function of these peptides is to destroy prokaryotic and other non-host cells by disrupting the cell membrane and promoting cell lysis. Common features of these naturally occurring amphipathic, lytic peptides include an overall basic charge, a small size (23–39 amino acid residues), and the ability to form amphipathic α-helices. Several types of amphipathic lytic peptides have been identified: cecropins (described in U.S. Pat. Nos. 4,355,104 and 4,520,016 to Hultmark et al.), defensins, sarcotoxins, melittin, and magainins (described in U.S. Pat. No. 4,810,777 to Zasloff). Each of these peptide types is distinguished by sequence and secondary structure characteristics.

Several hypotheses have been suggested for the mechanism of action of the lytic peptides: disruption of the membrane lipid bilayer by the amphipathic α-helix portion of the lytic peptide; lytic peptide formation of ion channels, which results in osmotically induced cytolysis; lytic peptide promotion of protein aggregation, which results in ion channel formation; and lytic peptide-induced release of phospholipids. Whatever the mechanism of lytic peptide-induced membrane damage, an ordered secondary conformation such as an α-amphipathic helix and positive charge density are features that appear to participate in the function of the lytic peptides.

Active analogs of naturally occurring lytic peptides have been produced and tested in vitro against a variety of prokaryotic and eukaryotic cell types (see for example Arrowood, M. J., et al. J. Protozool. 38: 161s [1991]; Jaynes, J. M., et al. FASEB J. 2: 2878 [1988]), including: gram positive and gram negative bacteria, fungi, yeast, envelope viruses, virus-infected eukaryotic cells, and neoplastic or transformed mammalian cells. The results from these studies indicate that many of the synthetic lytic peptide analogs have similar or higher levels of lytic activity for many different types of cells, compared to the naturally occurring forms. In addition, the peptide concentration required to lyse microbial pathogens such as protozoans, yeast, and bacteria does not lyse normal mammalian cells.

The specificity of the lytic action depends upon the sequence and structure of the peptide, the concentration of the peptide, and the type of membrane with which it interacts. Jaynes et al. Peptide Research. 2: 157 (1989) discuss the altered cytoskeletal characteristics of transformed or neoplastic mammalian cells that make them susceptible to lysis by the peptides. In these experiments, normal, human non-transformed cells remained unaffected at a given peptide concentration while transformed cells were lysed; However, when normal cells were treated with the cytoskeletal inhibitors cytochalasin D or colchicine, sensitivity to lysis increased. The experiments show that the action of lytic peptides on normal mammalian cells is limited. This resistance to lysis was most probably due to the well-developed cytoskeletal network of normal cells. In contrast, transformed cell lines which have well-known cytoskeletal deficiencies were sensitive to lysis. Because of differences in the sensitivity to lysis of microbial pathogens (high sensitivity), transformed mammalian cells (high sensitivity), and normal mammalian cells (resistant), amphipathic peptide concentration can be manipulated to effect lysis of one cell type but not another at the same locus.

Synthetic peptide analogs can also act as agents of eukaryotic cell proliferation. Amphipathic peptides that promote lysis of transformed cells will, at lower concentrations, promote cell proliferation in some cell types. This stimulatory activity is thought to depend on the channel-forming capability of the amphipathic peptides, which somehow stimulates nutrient uptake, calcium influx or metabolite release, thereby stimulating cell proliferation (see Jaynes, J. M. Drug News & Perspectives 3: 69 [1990]; and Reed, W. A. et al. Molecular Reproduction and Development 31: 106 [1992]). Thus, at a given concentration, these peptides stimulate or create channels that can be beneficial to the normal mammalian cell in a benign environment where it is not important to exclude toxic compounds.

The synthetic amphipathic peptide analogs typically contain as few as 15 and as many as 40 amino acid residues. A phenylalanine residue is often present at the amino terminus of the protein to provide an aromatic moiety analogous to the tryptophan residue located near the amino terminus of natural cecropins, and a UV-absorbing moiety with which to monitor the purification of the synthetic peptide. The basis for the design of these lytic peptide analogs is that an amphipathic peptide of minimal length and containing overall positive charge density effects lytic activity.

The foregoing facts suggest that although lytic peptides as a class may include species that are efficacious in destroying neoplastic cells, the concomitant mediative effect characteristic of lytic peptides, of promoting cell proliferation, would render such lytic peptides poor therapeutic agents for the treatment or prophylaxis of neoplastic conditions.

With respect to the incidence and prevalence of neoplasias, there has been significant attention focused on female cancers in recent years. According to the U.S. American Cancer Society 570,000 women in the United States in 1993 were anticipated to contract some form of cancer. The estimated death rate for women in that year was 249,000, of which 28% were projected to be attributable to breast, ovarian, uterine and cervical cancer. The incidence rates are much higher for the same group, exceeding the death rate for all cancers women. Recent research appears to indicate that other forms of cancer afflicting both men and women, such as lung cancer, may be distinct, and require different treatments from those conventionally available.

There has correspondingly been a growing awareness that insufficient focus and resources have been placed on finding effective treatments for cancers specific to women. This is especially true in the case of breast cancer, which alone claims the lives of nearly 50,000 women in the U.S. alone, and which appears to be increasing in incidence. In 1940, the incidence of breast cancer in the U.S. was 1 in 20 women; by 1993 the rate had increased to 1 in 9 women.

Correspondingly, during the 1970's and 1980's, other forms of women's cancers shows similarly alarming increases: kidney and renal carcinoma increased by 15.2%; melanoma of the skin by 21.3%; multiple myeloma by 25.8%; non-Hodgkin's lymphoma by 26.5%; and cancer of the larynx by 39.2%. During the same period, lung cancer increased 18% in men, while in women, the increase was 118.3%.

As the incidence of cancer in women under the age of 50 increases, there is a corresponding increasing and severe impact on society. Women in this age group not only serve as the primary caregivers to their children, they also have come to play an increasingly important role as support/caregivers to elderly parents, as well as comprising a substantial portion of the workforce. Thus, when a women under the age of 50 is stricken with cancer, it may adversely affect regenerations within her family.

Accordingly, it would be a significant advance in the art, and is correspondingly an object of the present invention to develop a method of combatting neoplastic conditions in mammalian subjects, utilizing a peptide agent which is lytically effective but non-proliferative of neoplastic cells or neoplastic tissue growth.

It is another object of the invention to provide novel peptide agents having utility for such method of combatting neoplastic conditions in mammalian subjects.

It is a further object of this invention to provide a method of combatting female mammalian neoplasias.

It is yet another object of the invention to provide a method of treating neoplasias in vivo, including female breast, ovarian, uterine and cervical cancers, by delivery of amphipathic non-naturally occurring peptides to neoplastic loci to effectively lyse transformed cells through peptide interaction with the cellular membrane.

Other objects and advantages will be more fully apparent from the ensuing disclosure and claims.

SUMMARY OF THE INVENTION

The present invention relates generally to a method of combatting, treating neoplastic conditions, comprising in vivo delivery to a corporeal neoplastic site of an effective amount of a non-naturally occurring, non-oncocytologically proliferative lytic peptide, and to peptides useful for such treatment, as hereinafter more fully described.

As used herein, the term "non-naturally occuring" means that the peptide or other species referred to, is a product of human agency and not a wild or otherwise naturally existing peptide.

As used herein, the term "non-oncocytologically proliferative lytic peptide" means a peptide which in vivo does not mediate or otherwise effect a net increase of more than 15% of the population of the neoplastic cells against which the peptide is lytically active. The proliferative effect of lytic peptides on the neoplastic cells can be readily determined within the skill of the art by suitable cellular count assays, e.g., utilizing a cytometer and suitable flow cytometry methods, relative to a corresponding control group of neoplastic cells under the same environmental conditions.

The term "amphipathic" as used herein in reference to peptide species means that the peptides have hydrophobic amino acid side chains which are oriented on one face or conformational region of the peptide, e.g., on one face of an alpha helix in the case of amphipathic α-helices as the peptide conformational structure, while the hydrophilic amino acid side chains are oriented on the other face or conformational region of the peptide. In more specific reference to α-helical peptides, the term "amphipathic" refers to the distribution of hydrophobic and hydrophilic amino acid residues along opposing faces of the α-helix structure, which results in one face of the α-helix structure being predominantly hydrophobic and the other face being predominantly hydrophilic. The degree of amphipathy of a peptide can be assessed by plotting the sequential amino acid residues on an Edmunson helical wheel.

In one specific aspect, the present invention relates to a method of treating neoplasias, comprising in vivo delivery of an effective amount of a non-naturally occurring, non-oncocytologically proliferative lytic peptide to a neoplastic locus.

The invention relates in a further aspect to an appertaining method of treating mammalian neoplasia disease states such as female cancers, including breast, ovarian, uterine, and cervical cancers, wherein a portion of the cells of the neoplastic locus are oncologically transformed and such peptide has a lytic effect on the transformed cells but not normal (i.e., non-oncologically transformed) cells.

The term "peptide" as used herein is intended to be broadly construed as inclusive of polypeptides per se having molecular weights of up to 10,000 daltons, as well as proteins having molecular weights of greater than about 10,000 daltons, wherein the molecular weights are number average molecular weights.

The term "methylated" as used herein means that the specified amino groups have been chemically reacted by a method of reductive alkylation or methylation so that the associated hydrogen atoms are replaced by covalently coupled methyl groups.

The term "glyoxylated" as used herein means that the specified guanido and α-amino groups have been chemically reacted such that each is covalently coupled to a glyoxal group.

As used herein, the terms "treating" or "combating" in reference to a physiological condition or disease state, is intended to be broadly construed as comprehending treatment of an existing condition or disease state, for amelioration thereof, as well as prophylactic treatment for prevention or diminution of the potential severity of such condition or disease state.

DETAILED DESCRIPTION OF THE INVENTION AND PREFERRED EMBODIMENTS THEREOF

Figure 1:
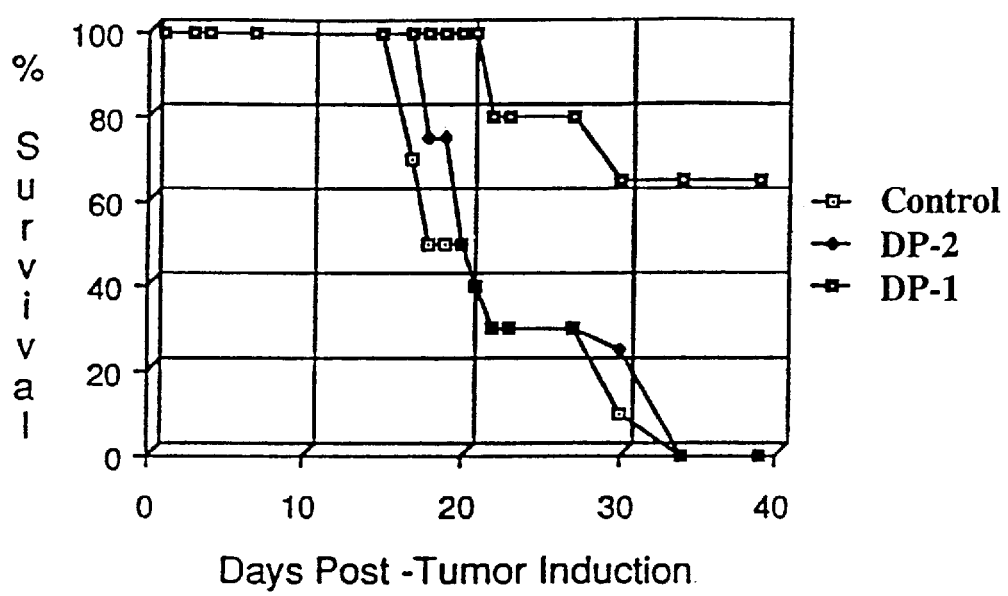
FIG. 1 is a graph of percentage survival of mouse melanoma cells as a function of time (days following tumor induction) for treatment of the melanoma cells with an amphipathic lytic peptide of Sequence ID No. 39 (as hereinafter described), DP-1, an amphipathic lytic peptide of Sequence ID No. 40 (as hereinafter described), DP-2, and a saline control (no lytic peptide treatment).

The disclosures of prior copending U.S. patent application Ser. No. 08/039,620 filed Jun. 4, 1993, now abandoned, in the names of Jesse M. Jaynes and Gordon R. Julian, U.S. patent application Ser. No. 08/148,889 filed Nov. 8, 1993, now abandoned, in the name of Gordon R. Julian, and U.S. patent application Ser. No. 08/148,491 filed Nov. 8, 1993, now abandoned, in the name of Gordon R. Julian, are all hereby incorporated herein by reference in their entirety.

The present invention provides a method of treating neoplasias and other oncocytological disease states, such as breast, ovarian, uterine, cervical, prostatic, dermal, and bronchogenic cancers, kidney and renal carcinomas, multiple myeloma, non-Hodgkins lymphoma, and laryngial cancer, that avoids many of the problems associated with current treatments and alternative approaches. The method of the present invention involves the use of lytic peptides which are "cytocidal", i.e., killingly effective, against neoplastic (transformed, cancerous) cells, attacking and destroying such cells while being non-cytocidal against normal (untransformed, non-cancerous) cells.

The invention contemplates the in vivo treatment of oncological conditions as well as the in vitro usage of lytic peptides for assay or analytical purposes. In corporeal (in vivo) usage, the lytic peptides of the present invention may be delivered to the corporeal neoplastic site by any suitable method of delivery efficacious therefor.

In the treatment of gastrointestinal neoplasias, e.g., of the stomach or intestinal tract, the peptides delivered to the gastrointestinal locus may be "latently lytic", i.e., non-lytic prior to action at the neoplastic site, but activated in vivo, under local conditions at the neoplastic site, so as not to affect normal gastrointestinal flora or metabolic order. Alternatively, the lytic peptides may be inherently stabilized proteolytically resistant (due to chemical modification) to accommodate oral delivery thereof. Peptides delivered to a neoplastic locus in active lytic form may usefully exhibit broad spectrum lytic activity for lysing pathogenic bacteria and virally infected cells, as well as transformed neoplastic cells, and thereby effect an enhanced therapeutic result.

Lytic peptides of the present invention are useful in treating animals, e.g., mammals such as humans, for conditions in which amelioration of cytologically manifested or mediated conditions such as neoplasia is desired, and against which the peptides are lytically effective.

A method of producing an antineoplastic response in an animal subject in need of such treatment comprises administering to the animal subject an antineoplasia-inducing amount of a composition including an effective lytic peptide which is non-oncocytologically proliferative in character.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered therapeutic composition containing lytic peptides of the invention at any suitable therapeutically effective and safe dosage, as may readily be determined within the skill of the art, and without undue experimentation.

In general, while the effective dosage of compounds of the invention for therapeutic use may be widely varied in the broad practice of the invention, depending on the specific application, (onoclogical) condition, or (neoplastic) disease state involved, as readily determinable within the skill of the art, suitable therapeutic doses of the active lytic peptide agent, as delivered to the targeted corporeal site, and for achievement of therapeutic benefit will generally be in the range of 0.05 to 15 milligrams (mg) per kilogram body weight of the recipient per day, preferably in the range of 0.10 $\mu$g to 5.0 mg per kilogram body weight per day, and most preferably in the range of 0.5 $\mu$g to 2.5 mg per kilogram body weight per day. The desired dose is preferably presented as two, three, four, five, six, or more sub-doses administered at appropriate intervals throughout the day. These sub-doses may be administered in unit dosage forms, for example, containing from 0.01 to 1.5 mg, and preferably from 0.025 to 1.25 mg of active ingredient per unit dosage form. Alternatively, if the condition of the recipient so requires, the doses may be administered as a continuous infusion, via iv perfusion, osmotic pump or transdermal delivery techniques, or by direct injection into the tumor (neoplastic) site.

The mode of administration and dosage forms will of course affect the therapeutic amounts of the compounds which are desirable and efficacious for the given treatment application.

For example, orally administered dosages (where the lytic peptide is stabilized, either inherently as synthesized or via post-formation modification, against proteolytic (e.g., gastric) e.g., digension by the modifications disclosed in prior copending U.S. patent application Ser. Nos. 08/148,889 and 08/148,491 filed Nov. 8, 1993, both now abandoned, the disclosures of which are hereby incorporated herein by reference, and such stabilized peptide is lytically active at the neoplastic site) typically are at least twice, e.g., 2–10 times, the dosage levels used in parenteral administration methods, for the same lytic peptide active ingredient. Intrathecal administration dosage levels generally are on the order of about 10% of the levels characteristic of parenteral administration dosage levels.

In general, administration levels of the lytic peptide therapeutic agents of the invention of more than about 15 milligrams per kilogram body weight per day are to be avoided, to maintain a conservative dosage level below the $ALD_{iv}$ of 40 milligrams per kilogram of body weight per day. It is noted that there is no determinate intramuscular approximate lethal dose ($ALD_{im}$). In preferred practice, the lytic peptide in a suitable formulation is administered by direct injection into the tumor, as a syringable composition efficacious for treatment of the neoplastic condition at the injection site. Alternatively, other direct modes of administration may be employed. For example, iv perfusion may be used to introduce the lytic peptide to the neoplastic site. As a further alternative, an osmotic pump may be placed in the vicinity of, or within, the tumor mass, and arranged to selectively release the lytic peptide, on a continuous, or non-continuous basis, to the neoplastic site.

In the case of cutaneous tumors, topical or transdermal delivery means and method may be employed, and in the case of cutaneous or subcutaneous tumors such transdermal means as transdermal patches may be utilized to deliver the lytic peptide to the neoplastic site.

The present invention also contemplates pharmaceutical formulations, both for veterinary and for human medical use, which comprise as the active agent one or more lytic peptide(s) of the invention, as well as the use of a lytic peptide of the invention in the manufacture of a medicament for the treatment or prophylaxis of the neoplastic conditions and/or other disease states variously described herein.

In such pharmaceutical and medicament formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, nasal, ophthalmic, subcutaneous, intramuscular, intravenous, transdermal, intrathecal, intra-articular, intra-arterial, subarachnoid, bronchial, lymphatic, and intra-uterine administration. Formulations suitable for parenteral administration are preferred.

When the active agent is utilized in a formulation comprising a liquid solution, the formulation advantageously may be administered parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously administered orally. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier which constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquid or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

The specific mode of delivery and administration of the lytic peptides of the present invention will depend on the specific corporeal site to be treated. In a given application, the optimum delivery route may differ depending on the form and stage of the cancer being treated. A generally useful route is intravenous administration, which is the route by which most chemotherapeutic drugs are administered at present. This administration route may be usefully employed, for example, for treatment of breast or uterine cancer, however intra-arterial administration may afford advantage as well in treatment of such types of cancer. Intra-arterial administration permits the introduction of the therapeutic agent(s) into the blood supply flowing directly to a tumor site, so that the agent(s) are delivered to the site prior to complete dilution in the total blood volume and prior to passage through the liver. In the case of ovarian cancer, intraperitoneal administration may usefully be employed, since the ovaries reside in the peritoneal cavity and are exposed directly to the fluid therein. For cervical cancer, direct injection into the uterine cervix may be usefully employed for delivery of the therapeutic agent(s), or alternatively a cervical cap used with a gel-form or other type composition containing the therapeutic agent(s) may be utilized.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

Usefulness of lytic peptides as cancer drugs depends upon their unique mechanism of action. Normal mammalian cells are resistant to lysis (cell death) due to their highly organized and well-developed cytoskeletal system. Cancerous cells, whether actively growing or dormant, are known to possess an inferior and compromised structure which when acted upon by the lytic peptides causes them to swell and burst. Hence, the killing of cancer cells while leaving normal cells unharmed, in the practice of the present invention, forms the basis for new chemotherapeutic cancer agents against cancers resistant to other forms of treatment.

The lysis is achieved by the assemblage of protein structures (membrane attack complexes) responsible for the lytic lesions formed in the lipid bilayers of cells of inferior cytoskeletal structure, such as cancer cells. The attack complex kills the cell by forming a tubule that traverses the membrane. This hollow cylinder, approximately 15 nm long and 10 nm in diameter, inserts its end into the lipid bilayer, and projects from it. A structure of this form perturbs the lipid bilayer sufficiently to allow for the free exchange of electrolytes and water across the membrane. The consequence of this action for a living cell is the net influx of sodium ions, calcium ions, and water due to the high internal colloid osmotic pressure. It is believed that one extremely small (10 nm) hole is sufficient to rapidly kill a single cell.

The features and advantages of the invention are more fully shown by the following illustrative examples and embodiments, which are not to be limitingly construed as regards the broad scope, utility, and applicability of the invention.

EXAMPLE 1

Representative Lytic Peptides

Set out in Table 1 below as illustrative examples of amphipathic peptide analogs of the present invention are the amino acid sequences of a family of related peptide analogs. The peptides may be synthesized according to conventional methods using a Milligen™ solid phase peptide synthesizer. Representative peptides from this group in some instances, are glyoxylated or methylated to stabilize same against proteolytic digestion, and used in subsequent experimental examples. The three letter amino acid symbols are as follows: Ala, alanine; Arg, arginine; Asp, aspartate; Gly, glycine; Ile, isoleucine; Leu, leucine; Lys, lysine; Phe, phenylalanine; and Val, valine. These amphipathic peptide analogs are designated for ease of reference as SEQ ID NO. 1–40.

TABLE 1

PEPTIDE SEQUENCES

SEQ ID NO: 1
Phe₁ Ala Val Ala Val₅ Lys Ala Val Lys Lys₁₀ Ala Val Lys Lys Val₁₅ Lys
Lys Ala Val Lys₂₀ Lys Ala Val Lys Lys₂₅ Lys Lys

SEQ ID NO: 2
Phe₁ Ala Val Ala Val₅ Lys Ala Val Ala Val₁₀ Lys Ala Val Lys Lys₁₅ Ala
Val Lys Lys Val₂₀ Lys Lys Ala Val Lys₂₅ Lys Ala Val Lys Lys₃₀ Lys Lys

SEQ ID NO: 3
Phe₁ Ala Val Ala Val₅ Lys Ala Val Ala Val₁₀ Lys Ala Val Ala Val₁₅ Lys
Ala Val Lys Lys₂₀ Ala Val Lys Lys Val₂₅ Lys Lys Ala Val Lys₃₀ Lys Ala
Val Lys Lys₃₅ Lys Lys

SEQ ID NO: 4
Phe₁ Ala Val Ala Val₅ Lys Ala Val Lys Lys₁₀ Ala Val Lys Lys Val₁₅ Lys
Lys Ala Val Lys₂₀ Lys Ala Val

SEQ ID NO: 5
Phe₁ Ala Val Ala Val₅ Lys Ala Val Ala Val₁₀ Lys Ala Val Lys Lys₁₅ Ala
Val Lys Lys Val₂₀ Lys Lys Ala Val Lys₂₅ Lys Ala Val

SEQ ID NO: 6
Phe₁ Ala Val Ala Val₅ Lys Ala Val Ala Val₁₀ Lys Ala Val Ala Val₁₅ Lys
Ala Val Lys Lys₂₀ Ala Val Lys Lys Val₂₅ Lys Lys Ala Val Lys₃₀ Lys Ala
Val

SEQ ID NO: 7
Phe₁ Ala Val Gly Leu₅ Arg Ala Ile Lys Arg₁₀ Ala Leu Lys Lys Leu₁₅ Arg
Arg Gly Val Arg₂₀ Lys Val Ala Lys Arg₂₅ Lys Arg

SEQ ID NO: 8
Phe₁ Ala Val Gly Leu₅ Arg Ala Ile Lys Arg₁₀ Ala Leu Lys Lys Leu₁₅ Arg
Arg Gly Val Arg₂₀ Lys Val Ala

SEQ ID NO: 9
Lys₁ Arg Lys Arg Ala₅ Val Lys Arg Val Gly₁₀ Arg Arg Leu Lys Lys₁₅ Leu
Ala Arg Lys Ile₂₀ Ala Arg Leu Gly Val₂₅ Ala Phe

SEQ ID NO: 10
Ala₁ Val Lys Arg Val₅ Gly Arg Arg Leu Lys₁₀ Lys Leu Ala Arg Lys₁₅ Ile
Ala Arg Leu Gly₂₀ Val Ala Phe

TABLE 1-continued

PEPTIDE SEQUENCES

SEQ ID NO: 11  Phe(1) Ala Val Gly Leu(5) Arg Ala Ile Lys Arg(10) Ala Leu Lys Lys Leu(15) Arg Arg Gly Val Arg(20) Lys Val Ala Lys Arg(25) Lys Arg Lys Asp Leu(30)

SEQ ID NO: 12  Phe(1) Ala Val Gly Leu(5) Arg Ala Ile Lys Arg(10) Ala Leu Lys Lys Leu(15) Arg Arg Gly Val Arg(20) Lys Val Ala Lys Asp(25) Leu

SEQ ID NO: 13  Lys(1) Arg Lys Arg Ala(5) Val Lys Arg Val Gly(10) Arg Arg Leu Lys Lys(15) Leu Ala Arg Lys Ile(20) Ala Arg Leu Gly Val(25) Ala Phe Lys Asp Leu(30)

SEQ ID NO: 14  Ala(1) Val Lys Arg Val(5) Gly Arg Arg Leu Lys(10) Leu Ala Arg Lys Ile(15) Ala Arg Leu Gly Val(20) Ala Phe Lys Asp Leu(25)

SEQ ID NO. 15:  Lys(1) Lys Lys Lys Phe(5) Val Lys Lys Val Ala(10) Lys Lys Val Lys Val(15) Ala Lys Lys Val(20) Ala Lys Val Ala Val(25) Ala Val

SEQ ID NO. 16:  Lys(1) Lys Lys Lys Phe(5) Val Lys Lys Val Ala(10) Lys Lys Val Lys Val(15) Ala Lys Lys Val(20) Ala Lys Val Ala Val(25) Ala Lys Val Ala Val(30) Ala Val

SEQ ID NO. 17:  Lys(1) Lys Lys Lys Phe(5) Val Lys Lys Val Ala(10) Lys Lys Val Lys Val(15) Ala Lys Lys Val(20) Ala Lys Val Ala Val(25) Ala Lys Val Ala Val(30) Ala Lys Val Ala Val(35) Ala Val

SEQ ID NO. 18:  Phe(1) Val Lys Lys Val(5) Ala Lys Lys Val Lys(10) Lys Val Ala Lys Lys(15) Val Ala Lys Val Ala(20) Val Ala Val

SEQ ID NO. 19:  Phe(1) Val Lys Lys Val(5) Ala Lys Lys Val Lys(10) Lys Val Ala Lys Lys(15) Val Ala Lys Val Ala(20) Val Ala Lys Val Ala(25) Val Ala Val

SEQ ID NO. 20:  Phe(1) Val Lys Lys Val(5) Ala Lys Lys Val Lys(10) Lys Val Ala Lys Lys(15) Val Ala Lys Val Ala(20) Val Ala Lys Val Ala(25) Val Ala Lys Val Ala(30) Val Ala Val

SEQ ID NO. 21:  Lys(1) Lys Lys Lys Phe(5) Val Lys Lys Val Ala(10) Lys Val Ala Lys Val(15) Ala Lys Val Ala(20) Lys Lys Val Ala Lys(25) Lys Val

SEQ ID NO. 22:  Lys(1) Lys Lys Lys Phe(5) Val Lys Lys Val Ala(10) Lys Val Ala Lys Val(15) Ala Lys Val Ala(20) Lys Lys Val Ala Lys(25) Lys Val Ala Lys Lys(30) Val Ala

SEQ ID NO. 23:  Lys(1) Lys Lys Lys Phe(5) Val Lys Lys Val Ala(10) Lys Val Ala Lys Val(15) Ala Lys Val Ala(20) Lys Lys Val Ala Lys(25) Lys Val Ala Lys Lys(30) Val Ala Lys Val Ala(35) Lys Lys

SEQ ID NO. 24:  Phe(1) Val Lys Lys Val(5) Ala Lys Val Ala Lys(10) Lys Val Ala Lys Val(15) Ala Lys Lys Val Ala(20) Lys Lys Val

SEQ ID NO. 25:  Phe(1) Val Lys Lys Val(5) Ala Lys Val Ala Lys(10) Lys Val Ala Lys Val(15) Ala Lys Lys Val Ala(20) Lys Lys Val Ala Lys(25)

TABLE 1-continued

PEPTIDE SEQUENCES

SEQ ID NO. 26:
Phe Val Lys Lys Val Ala Lys Val Ala Lys Lys Val Ala Lys Val Ala
1             5                 10              15
Lys Lys Val Ala Lys Lys Val Ala Lys Lys Val Ala Lys Val Ala Lys
            20              25              30
Lys

SEQ ID NO. 27:
Phe Val Lys Lys Val Ala Lys Val Ala Lys Lys Val Ala Lys Val Ala
1             5                 10              15
Lys Lys Val Ala Lys Lys Val Lys Lys Lys Lys
            20              25

SEQ ID NO. 28:
Phe Val Lys Lys Val Ala Lys Val Ala Lys Lys Val Ala Lys Val Ala
1             5                 10              15
Lys Lys Val Ala Lys Lys Val Ala Lys Lys Val Ala Lys Lys Lys
            20              25              30

SEQ ID NO. 29:
Phe Val Lys Lys Val Ala Lys Val Ala Lys Lys Val Ala Lys Val Ala
1             5                 10              15
Lys Lys Val Ala Lys Lys Val Ala Lys Lys Val Ala Lys Val Ala Lys
            20              25              30
Lys Lys Lys Lys Lys
        35

SEQ ID No. 30:
Phe Lys Val Lys Ala Lys Val Lys Ala Lys Val Lys Lys Lys Lys Lys
1             5                 10              15

SEQ ID NO. 31:
Phe Lys Val Lys Ala Lys Val Lys Ala Lys Val Lys Ala Lys Val Lys
1             5                 10              15
Ala Lys Lys Lys Lys
            20

SEQ ID NO. 32:
Phe Lys Val Lys Ala Lys Val Lys Ala Lys Val Lys Ala Lys Val Lys
1             5                 10              15
Ala Lys Val Lys Ala Lys Val Lys Lys Lys Lys
            20              25

SEQ ID NO. 33:
Phe Lys Val Lys Ala Lys Val Lys Ala Lys Val Lys
1             5                 10

SEQ ID NO. 34:
Phe Lys Val Lys Ala Lys Val Lys Ala Lys Val Lys Ala Lys Val Lys
1             5                 10              15
Ala

SEQ ID NO. 35:
Phe Lys Val Lys Ala Lys Val Lys Ala Lys Val Lys Ala Lys Val Lys
1             5                 10              15
Ala Lys Val Lys Ala Lys Val
            20

SEQ ID NO. 36:
Lys Lys Lys Lys Phe Lys Val Lys Ala Lys Val Lys Ala Lys Val Lys
1             5                 10              15

SEQ ID NO. 37:
Lys Lys Lys Lys Phe Lys Val Lys Ala Lys Val Lys Ala Lys Val Lys
1             5                 10              15
Ala Lys Val Lys Ala
            20

SEQ ID NO. 38:
Lys Lys Lys Lys Phe Lys Val Lys Ala Lys Val Lys Ala Lys Val Lys
1             5                 10              15
Ala Lys Val Lys Ala Lys Val Ala Lys Val
            20              25

SEQ ID NO. 39:
Phe Ala Leu Ala Leu Lys Ala Leu Lys Lys Ala Leu Lys Lys Leu
1             5                 10              15
Lys Lys Ala Leu Lys Lys Ala Leu
            20

SEQ ID NO. 40:
Leu Ala Lys Lys Leu Ala Lys Lys Leu Lys Lys Leu Ala Lys Lys
1             5                 10              15
Leu Ala Lys Leu Ala Leu Ala Phe
            20

Chemical modification of amphipathic peptide analogs offers certain advantages. If the modifications are made in such a way that the peptides retain all or most of their amphipathic characteristics, then the physiologically active peptides have enhanced stability to proteolysis. With enhanced stability, oral delivery of the peptide is advantageously accommodated without excessive loss of activity due to proteolytic digestion. The stabilized lytic peptides of such type are suitably stabilized so as to remain resistant to proteolysis so that the peptide reaches the neoplastic locus in an active condition. Alternatively, the lytic peptide may be originally synthesized in a stabilized form, or it may be chelated or otherwise coupled with an associated complexing agent so that the complexed peptide is initially nonlytically active in character, but under conditions existing at the neoplastic corporeal locus the complexed composition dissociates or otherwise "unbinds" to provide the lytically active peptide for antineoplastic activity at such locus.

Preferred antineoplastically effective lytic peptides within the general practice of the present invention include small (23–39 amino acid units) amphipathic cationic lytic peptides selected from those identified by amino acid sequence above which are non-oncocytologically proliferative in the specific neoplasia treatment application. The antineoplastically effective peptides of the invention are synthetic amphipathic lytic peptide analogs of melittin, cecropin, magainin, and defensin peptides. Most preferred are synthetic amphipathic lytic peptide analogs of melittin and cecropin peptides.

The lytic peptides of the present invention achieve their antineoplastic effect by causing severe perturbation of the cellular membranes of neoplastic (malignant) cells. The lytic peptides also exhibit concentration-dependent cell-proliferating, as well as neoplastic effects. The therapeutically useful peptides of the present invention selected for antineoplastic treatment are chosen to be non-oncocytologically proliferative in character, as is readily determinable within the skill of the art for a given neoplasia treatment application. Alterations in peptide charge density, hydrophobicity or length may affect the neoplastic and proliferative character of the peptide. The peptides of the invention have been designed to provide high antineoplastic activity and to minimize concentration-dependent proliferation of neoplastic cells. Generally, lytic peptide concentrations on the order of 1 nM to 1 $\mu$M are usefully employed, particularly in the treatment of female mammalian neoplasias.

Using an MTT assay in testing of lytic peptides of the invention against various neoplastic cell lines, including human breast cancer cell lines T47-D, MDA-231, and BT-474, osteosarcoma line MG-63, nasopharyngeal carcinoma line KB, and murine B16 melanoma, it has been determined that the synthetic analogs of melittin and cecropin peptides provide high levels of antineoplastic activity, having $IC_{50}$ values of 1.0 to 5.0 $\mu$M with variable stimulation of cell proliferation at lower concentrations.

EXAMPLE 2

Peptide Stabilization-Chemical Modification by Methylation

An exemplary and preferred reaction scheme for reductive alkylation of lysine residue ∈-amino group and the N-terminal $\alpha$-amino group is described below.

The preferred method for reductive alkylation uses pyridine borane as the reducing agent. This reagent is one of a class of reducing agents known as amine boranes. Pyridine borane exhibits a slightly higher reducing capacity than sodium cyanoborohydride, another reducing agent that can be used for the reductive alkylation. Pyridine borane drives the reductive alkylation reaction to complete dimethylation with no monomethyl products when excess reagents are used, as demonstrated by Wong, W. S. D., et al. Analytical Biochemistry 139: 58 (1984). While as much as 25% of cyanoborohydride goes to N-cyanomethyl products, lowering its methylation yield, pyridine borane does not appear to be involved in any such secondary reaction. In addition, sodium cyanoborohydride provides the potential hazard of contaminating the product with cyanide, severely limiting its use in therapeutic and in vivo applications. The alkylation reagent may suitably comprise formaldehyde as a methyl group (methylation) precursor. Shown below are the agents of reductive alkylation, formaldehyde and pyridine borane, the substrate, peptidyl lysine, and the chemical formulae of the reaction scheme species.

REACTION SCHEME 1

Dimethylation of Peptidyl Lysine

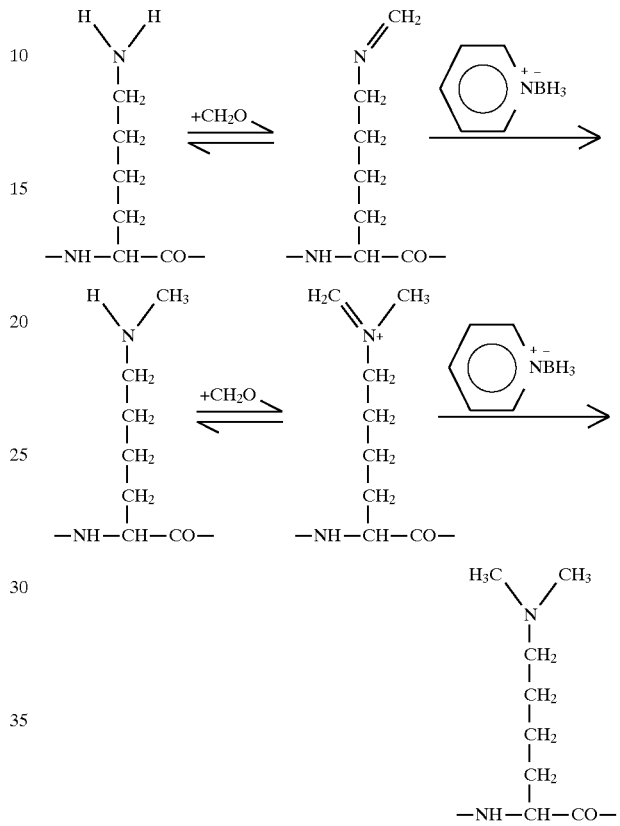

In the reductive alkylation reaction, 20 mg of a representative lysine containing peptide taken from the group shown in Table 1 was dissolved in 1.6 ml 0.2M HEPES buffer (N-2-hydroxyethylpiperazine-N'-2-ethane sulfonic acid), pH 7.0. While the mixture was stirring, 0.2 ml of 1.2M pyridine borane (0.750 concentrated pyridine borane in 5 ml HPLC grade methanol) was added. Next, 0.2 ml of 0.726M formaldehyde (0.6 ml 37% formaldehyde [HCHO] in 10 ml HEPES pH 7.0 buffer) was added to the mixture. A trace (approximately 1 $\mu$l) of 1-octanol was included in the reaction volume to control foaming. The reaction volume was then stirred for 2 hours at room temperature. After 2 hours the reaction mixture was titrated to below pH 3.0 with 0.2M HCl. The reaction mixture was then frozen and lyophilized to reduce volume, and the resulting residue was washed 3 times with anhydrous ether to remove the pyridine borane. The reaction residue was reconstituted to approximately 2.0 ml with 0.1M acetic acid and applied to a 2.4 cm×31 cm G-15–120$\mu$ Sephadex™ column to purify the reaction product. After the calibrated front eluted from the column (0.1M acetic acid was the elution reagent), 20 ml of eluate containing the product was collected and the eluate was lyophilized to dryness.

The peptides were stored at −20° C. in the presence of a desiccant as their acetate salt. For use in the following examples they are dissolved in a saline buffer, pH 7.0, at a concentration of 0.1 mg/ml to 10 mg/ml.

EXAMPLE 3

Peptide Stabilization-Chemical Modification by Glyoxylation

An exemplary and preferred reaction scheme for glyoxylation of the guanido groups of arginine residues and the N-terminal α-amino acid in a peptide taken from the group set out in Table 1 is described below.

Potential reagents which are capable of modifying the guanido group arginine with glyoxal under mild conditions and do not require an additional reduction reaction are 2,3-butanedione, phenylglyoxal, and glyoxal. The adducts from 2,3-butanedione and phenylglyoxal were judged to be too unstable, and glyoxal was therefore chosen as the preferred reagent for glyoxylation. The agent of glyoxylation, glyoxal, the substrate, peptidyl arginine, and the chemical reaction scheme are described below.

REACTION SCHEME 2

Glyoxylation of Peptidyl Arginine

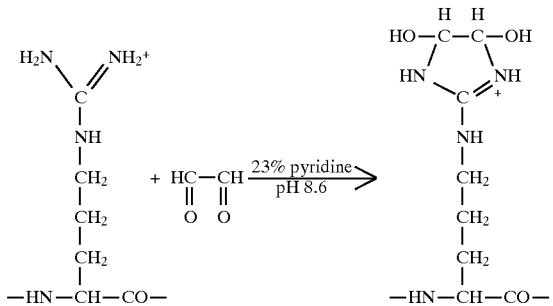

In the glyoxylation reaction, 5 mg of an arginine-containing peptide from the group shown in Table 1 was dissolved in 1.0 ml of 80% pyridine to form a clear solution. To this mixture 2 ml of 0.5M sodium bicarbonate buffer pH 8.0 ($NaHCO_3$—NaOH) was added. Freshly prepared, 30% glyoxal suspension in the 0.5M sodium bicarbonate buffer was added to the reaction volume and the cloudy reaction mixture was stirred at room temperature for three hours. After 20 minutes the solution became mostly clear although progressively yellow-brown during the course of the reaction. The final concentration of the pyridine was 23%. The pyridine, as a representative heterocyclic amine, was essential to the reaction, in order to maintain the glyoxal/peptide mixture in solution. Other water-soluble dielectric solvents such as the heterocyclic amine piperidine were tested and can be used in the place of pyridine.

At the conclusion of the reaction, glacial acetic acid was added drop-wise to bring the pH to 6.0. A two-phase extraction using three parts ether to one part acetone for the organic phase was repeated three times to remove the majority of the glyoxal. The pyridine was not removed to a significant extent. The preparation was dried in a lyophilizer and the crusty residue was rinsed with three parts ether to one part acetone. The residual ether-acetone was removed in vacuo. The cloudy ether-acetone supernatant was centrifuged to recover a precipitate which was pooled with the remaining residue by washing the tube with glacial acetic acid. The residue was dissolved in glacial acetic acid and a small amount of insoluble material was removed by centrifugation. The solution was then applied to a G-15–120 Sephadex™ column (2.4×31 cm) and eluted with 0.1M acetic acid. The recovered fraction were lyophilized to dryness overnight.

The peptides were stored at −20° C. in the presence of a desiccant as their acetate salt. For use in the following examples they were dissolved in a saline buffer, pH 7.0 at a concentration of 0.1 mg/ml to 10 mg/ml.

EXAMPLE 4

In Vitro Lysis of Pathogenic Bacteria

The effect of a lytic peptide (Hecate-1, homologous to SEQ ID NO. 4) was tested against antibiotic-resistant pathogenic bacteria in vitro. In this test, antibiotic-resistant cultures of *Pseudomonas aeruginosa* and *Klebsiella pneumoniae* were obtained from deceased patients. The lytic peptide bioassay was performed as described below.

A flask containing 49 ml of nutrient broth was inoculated with 1 ml of an overnight culture of the test bacteria. The culture was allowed to grow to mid-log phase at 37° C. with shaking (approximately 4 hours). When the cells reached the correct density, the cells were transferred to a sterile tube and centrifuged for 10 minutes at 3000 rpm. The pellet was resuspended in 3 ml of phosphate buffer and centrifuged for 10 minutes at 3000 rpm. The pellet was resuspended once again in sufficient (but measured) volume to calculate the absorbance of the suspension at 600 nm. Using the resulting absorbance and a previously constructed growth curve, the required dilution to achieve a concentration of $10^6$ cells/ml was determined.

One micromole of the test peptide was dissolved in 1.0 ml of 0.01 % acetic acid to make a 1 mM solution and serial dilutions were made to give a range of peptide concentrations from 10 $\mu$M to 1 mM. The test culture tubes for the bioassay contained 800 $\mu$l of phosphate buffer, pH 7.0, 100 $\mu$l of cells at $10^6$ cells/ml and 100 $\mu$l of peptide solution (10 $\mu$M to 1 mM). The final concentration of peptide in the assay was from 1 $\mu$M to 100 $\mu$M. A reaction system minus peptide was included as a control. The tubes were incubated at 37° C. for one hour.

After the incubation period, for each tube two 1:10 serial dilutions in phosphate buffer were made (three 1:10 serial dilutions for the control culture). 100 $\mu$l of each dilution was spread on an agar plate, in duplicate and incubated overnight at 37° C. The following day, the number of colonies on the control plates was counted to determine the starting number of cells in the assay tubes. The number of cells surviving the assay in the presence of peptide was also counted. The results are shown in Table 2.

TABLE 2

Lysis of Pathogenic Bacteria with Lytic Peptide

| Species | No. of Independent Isolates Tested | Average Minimal Inhibitory Concentration |
|---|---|---|
| *Pseudomonas aeruginosa* | 1 | 6.5 $\mu$M |
| *Klebsiella pneumoniae* | 4 | 9.9 $\mu$M |

The results show that a lytic peptide concentration in the range of 1 $\mu$M to 100 $\mu$M was effective for lysis of antibiotic resistant *Pseudomonas aeruginosa* and *Klebsiella pneumoniae*, most preferably in the range of 5 $\mu$M to 50 $\mu$M.

In a second experiment, antibiotic-resistant isolates of *Mycobacterium tuberculosis, Streptococcus pneumoniae, Pneumocystis carinii, Hemophilus influenzae, Klebsiella pneumoniae, Chlamydia pneumoniae,* and *Pseudomonas*

*cepacia* are tested in the same bioassay for lytic activity. Peptide concentration in the range of 1 μM to 100 μM is effective for lysis of the tested pathogenic bacteria, most preferably in the range of 5 μM to 50 μM. This concentration of peptide will be compared with the amount required to treat the pulmonary epithelial cells in a non-toxic manner in order to develop an effective combination dose for concurrent treatment of CF and accompanying bronchopulmonary infections, as well as other pulmonary diseases.

EXAMPLE 5

In Vitro Toxicity of Peptide to Epithelial Cells

A lytic peptide and a chemically modified non-lytic peptide selected from the group shown in Table 1 are tested in vitro with normal and cystic fibrosis affected lung and gastrointestinal epithelial cells, and the cells are assayed for survival. Cell culture is performed according to standard protocols (see for example Reed, W. A. et al. Molecular Reproduction and Development 31: 106 [1992]), and the cytotoxicity assay by $^{51}$Cr release is performed as in Jaynes, J. M. et al. Peptide Research 2: 157 (1989). This test shows a range of peptide concentration that is non-toxic for the cells in vitro. The purpose of the experiment is to formulate a range of safe doses of peptide for in vitro and in vivo experiments. Peptide concentration above 100 μM to 500 μM is toxic for the epithelial cells.

EXAMPLE 6

In Vitro Effectiveness of Chloride Conductance in CF Epithelial Cells

A lytic peptide and a chemically modified non-lytic peptide selected from the group shown in Table 1 are tested in vitro for stimulation of chloride efflux with pulmonary and gastrointestinal epithelial cells, using a range of peptide concentration that is non-toxic to the cells as shown by the experiments in Example 5. The peptides used in this experiment are chemically modified and non-lytic, for the gastrointestinal epithelial cells, and non-modified, lytic peptides for the pulmonary epithelial cells.

The rationale for this experiment is based on previous experiments for cell proliferation (see Reed, W. A. et al Molecular Reproduction and Development 31: 106 [1992]) which showed that for cultures of epithelial cells, application of peptide in the range of 10 μM to 50 μM stimulated cell growth. The hypothesis for the mechanism of cell growth is that the peptide caused the stimulation of alternative channels or the formation of new channels, providing for better passage of nutrients or metabolites. This hypothesis (e.g. channel formation or stimulation) is also suggested as the mechanism for stimulation of chloride efflux in normal and CF epithelial cells. The cells are cultured according to standard protocols as in Example 5, and chloride efflux is measured according to standard protocols.

Peptide concentration in the range of 1 μM to 50 μM is effective for stimulating chloride efflux from pulmonary and gastrointestinal epithelial cells. Combining the results of the pathogenic bacterial lysis experiment, the epithelial cell toxicity experiment, and the stimulation of chloride efflux experiment yields the following conclusion: a peptide concentration corresponding to 1 μM to 50 μM is the preferred range for treatment of CF affected epithelial cells, microbial infections and other disease states in vitro.

EXAMPLE 7

In Vivo Lysis of Pathogenic Bacteria in Infected Mice

The effect of a representative lytic peptide from the group shown in Table 1 is tested in mice that have bronchopulmonary infections of *Mycobacterium tuberculosis, Pseudomonas aeruginosa,* or *Pseudomonas cepacia.* Mice infected with both antibiotic-resistant and non-resistant bacteria are used, and treatment with antibiotics is compared to treatment with a lytic peptide. A concentration of peptide in the range of 10 μg to 25 mg per kg body weight for the recipient per day is the preferred range for treatment. The desired dose is preferably presented as two, three, four, five, six, or more sub-doses administered at appropriate intervals throughout the day. These sub-doses may be administered in unit dosage forms, for example containing from 10 μg to 1000 mg, preferably from 50 μg to 500 mg, and most preferably from 50 μg to 250 mg of active ingredient per unit dosage form.

An advantageous modality of in vivo pulmonary delivery of the peptide is via a liquid nebulizer inhaler device or a dry powder nebulizer inhaler device, depending on the physical state, solubility, and dosage of the peptide. Suitable nebulizers are commercially available under the trademarks "ROTAHALER", "SPINHALER", and "TURBOHALER". Another potentially suitable powder nebulizer apparatus and method of nebulization is disclosed in U.S. Pat. No. 5,186,166 to Riggs et al.

This experiment shows that peptide in the preferred range of 10 μg to 25 mg per kg body weight for the recipient per day is effective for treatment of mice with bronchopulmonary infections.

EXAMPLE 8

In Vivo Test of CF Mice Treated with Peptide at Pulmonary Site

The effect of a representative lytic, non-chemically modified peptide from Table 1 is tested on previously engineered transgenic mice that are homozygous for the CF defect. The peptide is delivered to a pulmonary locus as described in Example 7. A concentration of peptide in the range of 10 μg to 25 mg per kg body weight for the recipient per day is employed as the preferred range for treatment. The desired dose is preferably presented as two, three, four, five, six, or more sub-doses administered at appropriate intervals throughout the day. These sub-doses may be administered in unit dosage forms, for example containing from 10 μg to 1000 mg, preferably from 50 μg to 500 mg, and most preferably from 50 μg to 250 mg of active ingredient per unit dosage form.

The experiment shows that peptide in the preferred range of 10 μg to 25 mg per kg body weight for the recipient per day is effective for treatment of mice with bronchopulmonary infections.

EXAMPLE 9

In Vivo Test of CF Mice Treated with Modified Peptide at Gastrointestinal Site The effect of a representative non-lytic, chemically modified peptide from Table 1 is tested on previously engineered transgenic mice that are homozygous for the CF defect, as described in Example 8. The peptide is orally delivered to the gastrointestinal locus, and the chemical modification (glyoxylation or methylation) of the peptide confers enhanced proteolytic resistance, as described in Examples 2–3. A concentration of peptide in the range of 10 μg to 25 mg per kg body weight for the recipient per day is utilized as a preferred range for treatment. The desired dose is preferably presented as two, three, four, five, six, or more sub-doses administered at appropriate intervals throughout the day. These sub-doses may be administered in unit dosage forms, for example containing from 10 μg to 1000 mg, preferably from 50 μg to 500 mg, and most preferably from 50 μg to 250 mg of active ingredient per unit dosage form.

The experiment shows that peptide in the preferred range of 10 μg to 25 mg per kg body weight for the recipient per day is effective for treatment of mice with gastrointestinal problems due to CF.

Examples 4–9 described above, taken together, demonstrate that a non-toxic, effective dose of amphipathic peptide can be used to treat CF affected epithelia at pulmonary and gastrointestinal sites and resulting bronchopulmonary infections concurrently in vivo. In addition, various compounds of the present invention having appertaining therapeutic ability may be usefully employed in the treatment of other pulmonary disease states including: various neoplasias, bronchogenic cancers, pneumonia, bronchitis, bronchopulmonary viral infections, and bronchopulmonary microbial infections.

Further, the lytic peptides of the present invention may be usefully employed in the treatment of neoplasias as well as the concurrent treatment of other conditions for which the peptides are therapeutically useful, i.e., the administered peptide may effect neoplastic activity at the same time it is physiologically and/or pharmaceutically useful for the treatment of other conditions or disease states in the subject receiving treatment. Examples of such other conditions or disease states include microbial, parasitic and viral infections, dermal and subdermal wounds (as to which the peptide is healingly effective), etc.

The lytic peptides of the invention may suitably be utilized in combination with one another, as a mixture of selected different peptides, as well as in single peptide form. The use of multiple lytic peptide species may for example be beneficial when the neoplastic site contains multiple tumors of differing type, as to which different peptides of the invention are therapeutically effective.

EXAMPLE 10

Antineoplastic Activity—Mammalian Melanoma

In the following description, the peptide denoted DP-1 had the amino acid sequence identified hereinabove as SEQ. ID NO. 39 and the peptide denoted DP-2 had the amino acid sequence identified hereinabove as SEQ. ID NO. 40, and the control was saline.

Mouse melanoma cells were introduced onto the scapula of the test mice. Seventy two hours later, treatment was begun with ten mice in each treatment group. One group was administered DP-1 peptide, one group was administered DP-2 peptide, and the third group was administered saline control. Each treatment consisted of a 25 μg intraperitoneal injection of 0.1 ml volume once a day every other day for one week. Each mouse received four injections in total. As shown by the resulting data in FIG. 1, while the DP-2 group and the control group both showed death of all animals after 33 days, the DP-1 group maintained a 62% survival rate through the 38 day study.

EXAMPLE 11

Toxicity Determination—Lytic Peptides

In the following description, the peptide denoted DP-1 had the amino acid sequence identified hereinabove as SEQ. ID NO. 39, the peptide denoted DP-1m had the same amino acid sequence identified hereinabove as SEQ. ID NO. 39 but was fully methylated to stabilize same against proteolysis in accordance with the methylation procedure as described hereinabove, the peptide denoted D5-C had the amino acid sequence identified hereinabove as SEQ. ID NO. 9, and the peptide denoted D5-F had the same amino acid sequence identified hereinabove as SEQ. ID NO. 12.

In the following description, Riv=iv administration in rat, Rim=intramuscular administration in rat, Miv=iv administration in mouse, and Mim=intramuscular administration in mouse.

Lethality data and clinical observations were collected during the ALD evaluation of the peptides denoted D5-F, DP-1, DP-1m. The data presented below are complete for D5-F and DP-1. Since it was necessary to repeat the im assessment for DP-1 m, due to poor solubility at the concentration required for im administration, the im findings for DP-1 m are not presented below.

iv Assessment

For all three compounds, two replicates were performed with both mice and rats. In the first replicate, the animals (one animal/dose) were exposed to a range of doses, 10.0, 5.0, 2.5, 1.0, 0.5, 0.25, 0.1, 0.05, 0.025, and 0.01 μM. For the second replicate, the lethal dose was diluted to produce an intermediate dose between the lethal dose and the subsequent nonlethal dose.

Mice Lethality and Clinical Observations

Lethality

Replicate 1: D5F and DP1 were lethal at 10.0 μM, whereas DP1m was not lethal at the same dose. No lethality resulted at the lower concentrations of D5F, DP1, and DP1m.

Replicate 2: For D5F and DP1, the high dose was diluted to 7.5 μM for the second replicate. The doses administered were 7.5, 5.0, 1.0, 0.5, 0.25, 0.1, 0.05, 0.025, and 0.01 μM. D5F was lethal at 7.5 μM, whereas DP1 was not. DP1m was again not lethal to the mice over the treatment levels delivered.

The effects of the highest dose (lethal—D5F and DP1, nonlethal—DP1 m) were verified by dosing one animal with the effective or highest no effect concentration used in Replicate 1. In the case of D5F, the dose of 7.5 μM was used to verify lethality observed in Replicate 2. The mice treated with these compounds were previously exposed to the lowest dose 0.01 μM. The doses were the following: D5F, 7.5 μM; DP1, 10.0 μM; and DP1m, 10.0 μM. For all components, mice were dead within four hours after treatment.

The lethality for the two DP-1 m formulations evaluated are not conclusive as to toxicity of DP-1m in mice.

Clinical Observations

One mouse exposed to 10 μM DP1 m exhibited discoloration of the tail soon after dosing. In particular, the tails appeared to darken from the usual pink coloration to bluish purple. The appearance of the tail resembled a cyanotic condition. Later during the two-week postdosing period, the end of the tail of the animal exposed to 10 μM DP1m sloughed off and the remaining tail portion exhibited a blue-black coloration.

Rat Lethality and Clinical Observations

Lethality

Replicate 1: D5F, DP1, and DP1m were lethal at 10.0 $\mu$M. No lethality resulted at the lower concentrations.

Replicate 2: For all compounds, the high dose was diluted to 7.5 $\mu$M for the second replicate. The doses administered were 7.5, 5.0, 2.5, 1.0, 0.5. 0.25, and 0.1 $\mu$M. D5F, DP1, and DP1m were lethal at 7.5 $\mu$M and were not lethal at the lower doses.

The lethality of the high dose was verified by dosing one animal with the lethal dose determined by Replicate 1. The rats used for the evaluation were remaining from the original shipment and were naive for treatment. The doses were the following: D5F, 10.0 $\mu$M; DP1, 10.0 $\mu$M; and DP1m, 10.0 $\mu$M. For all compounds, the rats were dead within four hours after treatment.

Clinical Observations

Rats exposed to 2.5 and 5.0 $\mu$M D5F exhibited discoloration of the tail soon after dosing. In particular, the tails appeared to darken from the usual pink coloration to bluish purple. The appearance of the tail resembled a cyanotic condition. Later during the two-week postdosing period, the ends of the tails of the animals exposed to 2.5 and 5.0 $\mu$M of D5F sloughed off and the remaining tail portion exhibited a blue-black coloration.

Im Assessment

For D5F and DP1, two replicates were performed with rats. In the first replicate, the animals (one animal/dose) were exposed to a range of doses; 10.0, 1.0, 0.1, and 0.01 $\mu$M. The dose range used was smaller than that originally planned due to the availability of the compound to prepare an adequate amount of dosing solution.

Replicates 1 and 2: im administration of each compound produced no effects. No lethality or clinical observations were observed after dosing. Also, gross examination of the hind leg musculature at necropsy indicated no changes related to the im administration of the compounds.

Set out below in Table 2 below is a summary of the lethal concentration and clinical observations for peptides DP-1, DP-1m, D5-C, and D5-F.

| Peptide | [$\mu$M] T = 0 | $\mu$mol Riv | $\mu$g/dose | $\mu$mol Rim | $\mu$g/dose | $\mu$mol Miv | $\mu$g/dose |
|---|---|---|---|---|---|---|---|
| DP-1 | 7.5; 10.0 | 1.5 | 4,689.41 | not lethal | not lethal | 0.2 | 625.36 |
| DP-1m | 7.5; 10.0 | 1.5 | 5,139.41 | not lethal | not lethal | 0.2 | 685.36 |
| D5-C | 2.0; 2.5 | 0.4 | 1,269.78 | not lethal | not lethal | 0.05 | 158.72 |
| D5-F | 7.5 | 1.5 | 5,416.19 | not lethal | not lethal | 0.15 | 541.62 |

EXAMPLE 12

Antineoplastic Activity—Mammalian Melanoma

In the following description, the peptide denoted DP-1 had the amino acid sequence identified hereinabove as SEQ. ID NO. 39, the peptide denoted DP-1m had the same amino acid sequence identified hereinabove as SEQ. ID NO. 39 but was fully methylated to stabilize same against proteolysis in accordance with the methylation procedure as described hereinabove, the peptide denoted D5-C had the amino acid sequence identified hereinabove as SEQ. ID NO. 9, and the peptide denoted D5-F had the same amino acid sequence identified hereinabove as SEQ. ID NO. 12.

The above-identified peptides were tested in murine in vivo systems to determine the antineoplastic efficacy thereof, in accordance with a standard MTT assay to determine the resulting $ID_{50}$ values, with the results shown in Table 3 below.

TABLE 3

| Peptide Designation | Average MTT $ID_{50}$ Values in $\mu$M |
|---|---|
| DP-1 | 5.57 |
| DP-1m | 5.43 |
| D5-C | 5.32 |
| D5-F | 4.75 |

EXAMPLE 13

Antineoplastic Activity—Human Mammalian Neoplasias

Various peptides having sequences shown in Table 1 were tested for antineoplastic activity. The cells utilized in the testing with one exception (mouse melanoma cells) were human clinical isolates (obtained at University of North Carolina Memorial Hospital, Chapel Hill, N.C.) and were derived from the following tumors: MG-63—chemotherapy resistant osteosarcoma; T47D—hormone sensitive breast tumor; MDA-MB231—hormone insensitive breast tumor; BT474—hormone sensitive breast tumor; B16F1—mouse melanoma; and KBATCC—nasopharyngeal carcinoma.

The test procedure was a conventional MTT $ID_{50}$ assay. Tests were done in quadruplicate and data were tabulated for the average $\mu$M concentration necessary to achieve the $ID_{50}$ (ranging from about 2 to about 20 $\mu$g/ml).

The results of the testing of twenty different peptides numbered 1–20 is set out in Table V below, and Table IV sets out the identity of such peptides with reference to the amino acid sequences thereof, with reference to sequences listed in Table I hereof.

TABLE IV

| SEQ. ID NO., Table I | Peptide Number Referenced in Table V |
|---|---|
| 1 | 1 |
| 4 | 2 |
| 15 | 3 |
| 18 | 4 |
| 21 | 5 |
| 24 | 6 |
| 27 | 7 |
| 31 | 8 |
| 34 | 9 |
| 37 | 10 |
| 7 | 11 |
| 8 | 12 |
| 9 | 13 |
| 10 | 14 |
| 11 | 15 |
| 12 | 16 |
| 13 | 17 |
| 14 | 18 |
| 39[a] | 19 |
| 39[b] | 20 |

[a] this peptide was SEQ ID NO. 39 in an unmodified (non-stabilized against proteolysis) form thereof
[b] this peptide was SEQ ID NO. 39 in a modified fully methylated (stabilized against proteolysis) form thereof

TABLE V

| Peptides | MG-63 | T47D | MDA231 | BT474 | B16F1 | KBATCC | Average |
|---|---|---|---|---|---|---|---|
| 1 | 10.00 | 2.20 | 10.00 | 10.00 | 5.60 | 5.10 | 7.15 |
| 2 | 10.00 | 6.00 | 10.00 | 10.00 | 5.80 | 8.40 | 8.37 |
| 3 | 10.00 | 4.30 | 10.00 | 7.40 | 6.00 | 6.50 | 7.37 |
| 4 | 10.00 | 4.90 | 10.O0 | 7.50 | 5.80 | 5.60 | 7.30 |
| 5 | 10.00 | 6.20 | 10.00 | 10.00 | 10.00 | 9.60 | 9.30 |
| 6 | 10.00 | 6.30 | 10.00 | 10.00 | 10.00 | 10.00 | 9.38 |
| 7 | 10.00 | 6.20 | 10.O0 | 10.00 | 10.00 | 6.30 | 8.75 |
| 8 | 10.00 | 8.40 | 10.00 | 10.00 | 10.00 | 10.00 | 9.73 |
| 9 | 10.00 | 9.30 | 10.00 | 10.00 | 10.00 | 10.00 | 9.88 |
| 10 | 10.00 | 2.90 | 10.00 | 10.00 | 10.00 | 10.00 | 8.82 |
| 11 | 10.00 | 10.00 | 10.00 | 10.00 | 10.00 | 8.90 | 9.82 |
| 12 | 10.00 | 10.00 | 10.00 | 10.00 | 10.00 | 5.60 | 9.27 |
| 13 | 5.90 | 1.40 | 10.00 | 6.80 | 2.20 | 5.60 | 5.32 |
| 14 | 6.40 | 4.60 | 5.30 | 10.00 | 3.60 | 4.50 | 5.73 |
| 15 | 6.10 | 4.30 | 10.00 | 8.80 | 7.70 | 7.30 | 7.37 |
| 16 | 5.90 | 2.00 | 4.20 | 6.20 | 5.10 | 5.10 | 4.75 |
| 17 | 6.90 | 1.00 | 9.20 | 6.30 | 8.50 | 5.40 | 6.22 |
| 18 | 10.00 | 4.40 | 10.00 | 7.70 | 10.00 | 6.10 | 8.03 |
| 19 | 5.60 | 4.80 | 5.90 | 5.80 | 5.90 | 5.40 | 5.57 |
| 20 | 4.90 | 3.40 | 6.40 | 5.80 | 6.40 | 5.70 | 5.43 |
| Average | 8.59 | 5.13 | 9.05 | 8.62 | 7.63 | 7.06 | |

*Please note that the two individual best peptides are in the cross-hatched boxes
**The two overall best peptides are cross-hatched and surrounded by lines in the "Average" column
***The numbers are MTT ID50 values in $\mu$M peptide concentration. The values listed as 10 are actually greater than 10.

The present invention also contemplates pharmaceutical formulations for human medical use, which comprise as one of the active agents therapeutic amounts of the peptides of Table 1 above as well as other physiologically active compounds. These formulations may for example include as additional components nebulizable compounds such as Survanta® TA pulmonary surfactant (Burroughs Wellcome Co.), Mucomist™ mucolytic agent (Mead-Johnson), Ribavirin™ virazole (TCN Pharmaceuticals), and DNase (Genentech), as well as other physiologically active therapeutic agents such as antibiotics.

While the invention has been described herein, with respect to certain features, aspects, and embodiments, it will be recognized that the invention may be widely varied, and that numerous other modifications, variations, and other embodiments are possible, and that such modifications, variations, and other embodiments are to be regarded as being within the spirit and scope of the invention.

What is claimed is:

1. A method of combatting mammalian neoplasia in a mammalian subject in need of such treatment, comprising administering to the subject an effective amount of a composition comprising a non-naturally occurring, anti-neoplastically effective, non-oncocytologically proliferative lytic peptide, wherein the peptide is selected from SEQ ID Nos. 1–3, 5–38 and 40.

2. A method according to claim 1, wherein the mammalian subject is a human subject.

3. A method according to claim 1, wherein the mammalian subject is a human female subject.

4. A method according to claim 3, wherein the neoplasia is selected from the group consisting of breast, ovarian, uterine and cervical neoplasias.

5. A method according to claim 1, wherein the effective amount of the lytic peptide is from about 0.05 milligram/kilogram body weight of the subject/day to 15.0 milligram/kilogram of body weight of the subject/day.

6. A method according to claim 1, wherein the lytic peptide is non-cytocidal against untransformed, non-cancerous cells.

7. A medicament for the treatment of neoplasia conditions comprising a non-naturally occurring, anti-neoplastically effective, non-oncocytologically proliferative lytic peptide, wherein the peptide is selected from SEQ ID NOs. 1–3, 5–38 and 40.

* * * * *

SEQUENCE LISTING ( 1 ) GENERAL INFORMATION:

( i i i ) NUMBER OF SEQUENCES: 40

( 2 ) INFORMATION FOR SEQ ID NO: 1:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 1:

Phe Ala Val Ala Val Lys Ala Val Lys Lys Ala Val Lys Lys Val Lys
1                             5                             10                        15

Lys Ala Val Lys Lys Ala Val Lys Lys Lys Lys
                 20                         25

( 2 ) INFORMATION FOR SEQ ID NO: 2:

( i ) SEQUENCE CHARACTERISTICS:
        ( A ) LENGTH: 32
        ( B ) TYPE: AMINO ACID (C) TOPOLOGY: LINEAR (i i) MOLECULE TYPE:
    (A) DESCRIPTION: PEPTIDE (i i i) HYPOTHETICAL: NO (v) FRAGMENT TYPE: COMPLETE PEPTIDE (v i) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 2:

```
Phe Ala Val Ala Val Lys Ala Val Ala Val Lys Ala Val Lys Lys Ala
 1               5                  10                  15
Val Lys Lys Val Lys Lys Ala Val Lys Lys Ala Val Lys Lys Lys Lys
                20                  25                  30
```

(2) INFORMATION FOR SEQ ID NO: 3:

(i) SEQUENCE CHARACTERISTICS:
    (A) LENGTH: 37
    (B) TYPE: AMINO ACID
    (C) TOPOLOGY: LINEAR (i i) MOLECULE TYPE:
    (A) DESCRIPTION: PEPTIDE (i i i) HYPOTHETICAL: NO (v) FRAGMENT TYPE: COMPLETE PEPTIDE (v i) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 3:

```
Phe Ala Val Ala Val Lys Ala Val Ala Val Lys Ala Val Ala Val Lys
 1               5                  10                  15
Ala Val Lys Lys Ala Val Lys Lys Val Lys Lys Ala Val Lys Lys Ala
                20                  25                  30
Val Lys Lys Lys Lys
                35
```

(2) INFORMATION FOR SEQ ID NO: 4:

(i) SEQUENCE CHARACTERISTICS:
    (A) LENGTH: 23
    (B) TYPE: AMINO ACID
    (C) TOPOLOGY: LINEAR (i i) MOLECULE TYPE:
    (A) DESCRIPTION: PEPTIDE (i i i) HYPOTHETICAL: NO (v) FRAGMENT TYPE: COMPLETE PEPTIDE (v i) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 4:

```
Phe Ala Val Ala Val Lys Ala Val Lys Lys Ala Val Lys Lys Val Lys
 1               5                  10                  15
```

Lys Ala Val Lys Lys Ala Val
            20

( 2 ) INFORMATION FOR SEQ ID NO: 5:

( i ) SEQUENCE CHARACTERISTICS:
         ( A ) LENGTH: 28
         ( B ) TYPE: AMINO ACID
         ( C ) TOPOLOGY: LINEAR ( i i ) MOLECULE TYPE:
         ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 5:

Phe Ala Val Ala Val Lys Ala Val Ala Val Lys Ala Val Lys Lys Ala
1               5                   10                  15
Val Lys Lys Val Lys Lys Ala Val Lys Lys Ala Val
            20                  25

( 2 ) INFORMATION FOR SEQ ID NO: 6:

( i ) SEQUENCE CHARACTERISTICS:
         ( A ) LENGTH: 33
         ( B ) TYPE: AMINO ACID
         ( C ) TOPOLOGY: LINEAR ( i i ) MOLECULE TYPE:
         ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 6:

Phe Ala Val Ala Val Lys Ala Val Ala Val Lys Ala Val Ala Val Lys
1               5                   10                  15
Ala Val Lys Lys Ala Val Lys Lys Val Lys Lys Ala Val Lys Lys Ala
            20                  25                  30
Val ( 2 ) INFORMATION FOR SEQ ID NO: 7:

( i ) SEQUENCE CHARACTERISTICS:
         ( A ) LENGTH: 27
         ( B ) TYPE: AMINO ACID
         ( C ) TOPOLOGY: LINEAR ( i i ) MOLECULE TYPE:
         ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 7:

```
Phe Ala Val Gly Leu Arg Ala Ile Lys Arg Ala Leu Lys Lys Leu Arg
1               5                   10                  15
Arg Gly Val Arg Lys Val Ala Lys Arg Lys Arg
                20                  25
```

(2) INFORMATION FOR SEQ ID NO: 8:

(i) SEQUENCE CHARACTERISTICS:
        (A) LENGTH: 23
        (B) TYPE: AMINO ACID
        (C) TOPOLOGY: LINEAR (i i) MOLECULE TYPE:
        (A) DESCRIPTION: PEPTIDE (i i i) HYPOTHETICAL: NO (v) FRAGMENT TYPE: COMPLETE PEPTIDE (v i) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 8:

```
Phe Ala Val Gly Leu Arg Ala Ile Lys Arg Ala Leu Lys Lys Leu Arg
1               5                   10                  15
Arg Gly Val Arg Lys Val Ala
                20
```

(2) INFORMATION FOR SEQ ID NO: 9:

(i) SEQUENCE CHARACTERISTICS:
        (A) LENGTH: 27
        (B) TYPE: AMINO ACID
        (C) TOPOLOGY: LINEAR (i i) MOLECULE TYPE:
        (A) DESCRIPTION: PEPTIDE (i i i) HYPOTHETICAL: NO (v) FRAGMENT TYPE: COMPLETE PEPTIDE (v i) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 9:

```
Lys Arg Lys Arg Ala Val Lys Arg Val Gly Arg Arg Leu Lys Lys Leu
1               5                   10                  15
Ala Arg Lys Ile Ala Arg Leu Gly Val Ala Phe
                20                  25
```

(2) INFORMATION FOR SEQ ID NO: 10:

(i) SEQUENCE CHARACTERISTICS:
        (A) LENGTH: 23
        (B) TYPE: AMINO ACID
        (C) TOPOLOGY: LINEAR (i i) MOLECULE TYPE:

(A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 10:

```
Ala  Val  Lys  Arg  Val  Gly  Arg  Arg  Leu  Lys  Lys  Leu  Ala  Arg  Lys  Ile
 1              5                        10                       15
Ala  Arg  Leu  Gly  Val  Ala  Phe
               20
```

(2) INFORMATION FOR SEQ ID NO: 11:

(i) SEQUENCE CHARACTERISTICS:
              (A) LENGTH: 30
              (B) TYPE: AMINO ACID
              (C) TOPOLOGY: LINEAR (ii) MOLECULE TYPE:
              (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 11:

```
Phe  Ala  Val  Gly  Leu  Arg  Ala  Ile  Lys  Arg  Ala  Leu  Lys  Lys  Leu  Arg
 1              5                        10                       15
Arg  Gly  Val  Arg  Lys  Val  Ala  Lys  Arg  Lys  Arg  Lys  Asp  Leu
               20                       25                       30
```

(2) INFORMATION FOR SEQ ID NO: 12:

(i) SEQUENCE CHARACTERISTICS:
              (A) LENGTH: 26
              (B) TYPE: AMINO ACID
              (C) TOPOLOGY: LINEAR (ii) MOLECULE TYPE:
              (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 12:

```
Phe  Ala  Val  Gly  Leu  Arg  Ala  Ile  Lys  Arg  Ala  Leu  Lys  Lys  Leu  Arg
 1              5                        10                       15
Arg  Gly  Val  Arg  Lys  Val  Ala  Lys  Asp  Leu
               20                       25
```

(2) INFORMATION FOR SEQ ID NO: 13:

(i) SEQUENCE CHARACTERISTICS:
    (A) LENGTH: 30
    (B) TYPE: AMINO ACID
    (C) TOPOLOGY: LINEAR (ii) MOLECULE TYPE:
    (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 13:

Lys Arg Lys Arg Ala Val Lys Arg Val Gly Arg Arg Leu Lys Lys Leu
 1               5                  10                 15
Ala Arg Lys Ile Ala Arg Leu Gly Val Ala Phe Lys Asp Leu
              20                  25                  30

(2) INFORMATION FOR SEQ ID NO: 14:

(i) SEQUENCE CHARACTERISTICS:
    (A) LENGTH: 26
    (B) TYPE: AMINO ACID
    (C) TOPOLOGY: LINEAR (ii) MOLECULE TYPE:
    (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 14:

Ala Val Lys Arg Val Gly Arg Arg Leu Lys Lys Leu Ala Arg Lys Ile
 1               5                  10                 15
Ala Arg Leu Gly Val Ala Phe Lys Asp Leu
              20                  25

(2) INFORMATION FOR SEQ ID NO: 15:

(i) SEQUENCE CHARACTERISTICS:
    (A) LENGTH: 27
    (B) TYPE: AMINO ACID
    (C) TOPOLOGY: LINEAR (ii) MOLECULE TYPE:
    (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 15:

Lys Lys Lys Lys Phe Val Lys Lys Val Ala Lys Lys Val Lys Lys Val

```
                1                    5                      1 0                           1 5
A l a   L y s   L y s   V a l   A l a   L y s   V a l   A l a   V a l   A l a   V a l
                            2 0                         2 5
```

( 2 ) INFORMATION FOR SEQ ID NO: 16:

( i ) SEQUENCE CHARACTERISTICS:
        ( A ) LENGTH: 32
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 16:

```
L y s   L y s   L y s   L y s   P h e   V a l   L y s   L y s   V a l   A l a   L y s   L y s   V a l   L y s   L y s   V a l
1                                   5                                       1 0                                      1 5
A l a   L y s   L y s   V a l   A l a   L y s   V a l   A l a   V a l   A l a   L y s   V a l   A l a   V a l   A l a   V a l
                            2 0                                      2 5                                      3 0
```

( 2 ) INFORMATION FOR SEQ ID NO: 17:

( i ) SEQUENCE CHARACTERISTICS:
        ( A ) LENGTH: 37
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 17:

```
L y s   L y s   L y s   L y s   P h e   V a l   L y s   L y s   V a l   A l a   L y s   L y s   V a l   L y s   L y s   V a l
1                                   5                                       1 0                                      1 5
A l a   L y s   L y s   V a l   A l a   L y s   V a l   A l a   V a l   A l a   L y s   V a l   A l a   V a l   A l a   L y s
                            2 0                                      2 5                                      3 0
V a l   A l a   V a l   A l a   V a l
                    3 5
```

( 2 ) INFORMATION FOR SEQ ID NO: 18:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE (v i) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 18:

Phe Val Lys Lys Val Ala Lys Lys Val Lys Lys Val Ala Lys Lys Val
1               5                   10                  15
Ala Lys Val Ala Val Ala Val
            20

(2) INFORMATION FOR SEQ ID NO: 19:

(i) SEQUENCE CHARACTERISTICS:
 (A) LENGTH: 28
 (B) TYPE: AMINO ACID
 (C) TOPOLOGY: LINEAR (i i) MOLECULE TYPE:
 (A) DESCRIPTION: PEPTIDE (i i i) HYPOTHETICAL: NO (v) FRAGMENT TYPE: COMPLETE PEPTIDE (v i) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 19:

Phe Val Lys Lys Val Ala Lys Lys Val Lys Lys Val Ala Lys Lys Val
1               5                   10                  15
Ala Lys Val Ala Val Ala Lys Val Ala Val Ala Val
            20                  25

(2) INFORMATION FOR SEQ ID NO: 20:

(i) SEQUENCE CHARACTERISTICS:
 (A) LENGTH: 33
 (B) TYPE: AMINO ACID
 (C) TOPOLOGY: LINEAR (i i) MOLECULE TYPE:
 (A) DESCRIPTION: PEPTIDE (i i i) HYPOTHETICAL: NO (v) FRAGMENT TYPE: COMPLETE PEPTIDE (v i) ORIGINAL SOURCE: SYNTHETIC (v i i) IMMEDIATE SOURCE: SYNTHETIC (x) PUBLICATION INFORMATION: NOT PREVIOUSLY PUBLISHED (x i) SEQUENCE DESCRIPTION: SEQ ID NO: 20:

Phe Val Lys Lys Val Ala Lys Lys Val Lys Lys Val Ala Lys Lys Val
1               5                   10                  15
Ala Lys Val Ala Val Ala Lys Val Ala Val Ala Lys Val Ala Val Ala
            20                  25                  30
Val (2) INFORMATION FOR SEQ ID NO: 21:

(i) SEQUENCE CHARACTERISTICS:
 (A) LENGTH: 27

(B) TYPE: AMINO ACID
(C) TOPOLOGY: LINEAR (ii) MOLECULE TYPE:
(A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 21:

Lys Lys Lys Lys Phe Val Lys Lys Val Ala Lys Val Ala Lys Lys Val
 1               5                   10                  15
Ala Lys Val Ala Lys Lys Val Ala Lys Lys Val
            20                  25

(2) INFORMATION FOR SEQ ID NO: 22:

(i) SEQUENCE CHARACTERISTICS:
(A) LENGTH: 32
(B) TYPE: AMINO ACID
(C) TOPOLOGY: LINEAR (ii) MOLECULE TYPE:
(A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 22:

Lys Lys Lys Lys Phe Val Lys Lys Val Ala Lys Val Ala Lys Lys Val
 1               5                   10                  15
Ala Lys Val Ala Lys Lys Val Ala Lys Lys Val Ala Lys Lys Val Ala
            20                  25                  30

(2) INFORMATION FOR SEQ ID NO: 23:

(i) SEQUENCE CHARACTERISTICS:
(A) LENGTH: 37
(B) TYPE: AMINO ACID
(C) TOPOLOGY: LINEAR (ii) MOLECULE TYPE:
(A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 23:

Lys Lys Lys Lys Phe Val Lys Lys Val Ala Lys Val Ala Lys Lys Val
 1               5                   10                  15
Ala Lys Val Ala Lys Lys Val Ala Lys Lys Val Ala Lys Lys Val Ala

```
                        20                        25                        30
Lys Val Ala Lys Lys
            35
```

(2) INFORMATION FOR SEQ ID NO: 24:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 24:

```
Phe Val Lys Lys Val Ala Lys Val Ala Lys Val Ala Lys Val Ala
1               5                   10                  15
Lys Lys Val Ala Lys Lys Val
            20
```

(2) INFORMATION FOR SEQ ID NO: 25:

(i) SEQUENCE CHARACTERISTICS:
        (A) LENGTH: 28
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 25:

```
Phe Val Lys Lys Val Ala Lys Val Ala Lys Lys Val Ala Lys Val Ala
1               5                   10                  15
Lys Lys Val Ala Lys Lys Val Ala Lys Lys Val Ala
            20                  25
```

(2) INFORMATION FOR SEQ ID NO: 26:

(i) SEQUENCE CHARACTERISTICS:
        (A) LENGTH: 33
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 26:

Phe Val Lys Lys Val Ala Lys Val Ala Lys Lys Val Ala Lys Val Ala
1               5                   10                  15

Lys Lys Val Ala Lys Lys Val Ala Lys Lys Val Ala Lys Val Ala Lys
            20                  25                  30

Lys ( 2 ) INFORMATION FOR SEQ ID NO: 27:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 27:

Phe Val Lys Lys Val Ala Lys Val Ala Lys Lys Val Ala Lys Val Ala
1               5                   10                  15

Lys Lys Val Ala Lys Lys Val Lys Lys Lys Lys
            20                  25

( 2 ) INFORMATION FOR SEQ ID NO: 28:

( i ) SEQUENCE CHARACTERISTICS:
        ( A ) LENGTH: 32
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 28:

Phe Val Lys Lys Val Ala Lys Val Ala Lys Lys Val Ala Lys Val Ala
1               5                   10                  15

Lys Lys Val Ala Lys Lys Val Ala Lys Lys Val Ala Lys Lys Lys Lys
            20                  25                  30

( 2 ) INFORMATION FOR SEQ ID NO: 29:

( i ) SEQUENCE CHARACTERISTICS:
        ( A ) LENGTH: 37
        ( B ) TYPE: AMINO ACID
        ( C ) TOPOLOGY: LINEAR (ii) MOLECULE TYPE:
    (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 29:

```
Phe Val Lys Lys Val Ala Lys Val Ala Lys Lys Val Ala Lys Val Ala
 1               5                  10                  15
Lys Lys Val Ala Lys Lys Val Ala Lys Lys Val Ala Lys Val Ala Lys
                20                  25                  30
Lys Lys Lys Lys Lys
                35
```

(2) INFORMATION FOR SEQ ID NO: 30:

(i) SEQUENCE CHARACTERISTICS:
    (A) LENGTH: 16
    (B) TYPE: AMINO ACID
    (C) TOPOLOGY: LINEAR (ii) MOLECULE TYPE:
    (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 30:

```
Phe Lys Val Lys Ala Lys Val Lys Ala Lys Val Lys Lys Lys Lys Lys
 1               5                  10                  15
```

(2) INFORMATION FOR SEQ ID NO: 31:

(i) SEQUENCE CHARACTERISTICS:
    (A) LENGTH: 21
    (B) TYPE: AMINO ACID
    (C) TOPOLOGY: LINEAR (ii) MOLECULE TYPE:
    (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 31:

```
Phe Lys Val Lys Ala Lys Val Lys Ala Lys Val Lys Ala Lys Val Lys
 1               5                  10                  15
Ala Lys Lys Lys Lys
                20
```

( 2 ) INFORMATION FOR SEQ ID NO: 32:

( i ) SEQUENCE CHARACTERISTICS:
    ( A ) LENGTH: 27
    ( B ) TYPE: AMINO ACID
    ( C ) TOPOLOGY: LINEAR ( i i ) MOLECULE TYPE:
    ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 32:

```
Phe Lys Val Lys Ala Lys Val Lys Ala Lys Val Lys Ala Lys Val Lys
 1               5                  1 0                 1 5
Ala Lys Val Lys Ala Lys Val Lys Lys Lys Lys
            2 0                 2 5
```

( 2 ) INFORMATION FOR SEQ ID NO: 33:

( i ) SEQUENCE CHARACTERISTICS:
    ( A ) LENGTH: 12
    ( B ) TYPE: AMINO ACID
    ( C ) TOPOLOGY: LINEAR ( i i ) MOLECULE TYPE:
    ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 33:

```
Phe Lys Val Lys Ala Lys Val Lys Ala Lys Val Lys
 1               5                  1 0
```

( 2 ) INFORMATION FOR SEQ ID NO: 34:

( i ) SEQUENCE CHARACTERISTICS:
    ( A ) LENGTH: 17
    ( B ) TYPE: AMINO ACID
    ( C ) TOPOLOGY: LINEAR ( i i ) MOLECULE TYPE:
    ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 34:

```
Phe Lys Val Lys Ala Lys Val Lys Ala Lys Val Lys Ala Lys Val Lys
 1               5                  1 0                 1 5
```

Ala ( 2 ) INFORMATION FOR SEQ ID NO: 35:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 35:

Phe Lys Val Lys Ala Lys Val Lys Ala Lys Val Lys Ala Lys Val Lys
1                  5                        10                     15

Ala Lys Val Lys Ala Lys Val
             20

( 2 ) INFORMATION FOR SEQ ID NO: 36:

( i ) SEQUENCE CHARACTERISTICS:
        ( A ) LENGTH: 16
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 36:

Lys Lys Lys Lys Phe Lys Val Lys Ala Lys Val Lys Ala Lys Val Lys
1                  5                        10                     15

( 2 ) INFORMATION FOR SEQ ID NO: 37:

( i ) SEQUENCE CHARACTERISTICS:
        ( A ) LENGTH: 21
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 37:

Lys Lys Lys Lys Phe Lys Val Lys Ala Lys Val Lys Ala Lys Val Lys
1               5                   10                  15
Ala Lys Val Lys Ala
            20

( 2 ) INFORMATION FOR SEQ ID NO: 38:

( i ) SEQUENCE CHARACTERISTICS:
        ( A ) LENGTH: 27
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 38:

Lys Lys Lys Lys Phe Lys Val Lys Ala Lys Val Lys Ala Lys Val Lys
1               5                   10                  15
Ala Lys Val Lys Ala Lys Val Lys Ala Lys Val
            20                  25

( 2 ) INFORMATION FOR SEQ ID NO: 39:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 39:

Phe Ala Leu Ala Leu Lys Ala Leu Lys Lys Ala Leu Lys Lys Leu Lys
1               5                   10                  15
Lys Ala Leu Lys Lys Ala Leu
            20

( 2 ) INFORMATION FOR SEQ ID NO: 40:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 40:

| Leu | Ala | Lys | Lys | Leu | Ala | Lys | Lys | Leu | Lys | Lys | Leu | Ala | Lys | Lys | Leu |
|---|---|---|---|---|---|---|---|---|---|---|---|---|---|---|---|
| 1 | | | | 5 | | | | | 10 | | | | | 15 | |

| Ala | Lys | Leu | Ala | Leu | Ala | Phe |
|---|---|---|---|---|---|---|
| | | | 20 | | | |